United States Patent [19]

Bonaldo et al.

[11] Patent Number: 5,702,898
[45] Date of Patent: Dec. 30, 1997

[54] PROCEDURE FOR NORMALIZATION OF CDNA LIBRARIES

[75] Inventors: Maria DeFatima Bonaldo; Marcelo Bento Soares, both of New York, N.Y.

[73] Assignee: The Trustees of Columbia University in The City of New York, New York, N.Y.

[21] Appl. No.: 465,857

[22] Filed: Jun. 6, 1995

[51] Int. Cl.$^6$ .............................. C12Q 1/68; C12P 19/34; C12N 15/00; C07H 21/00

[52] U.S. Cl. .............. 435/6; 435/91.51; 435/172.3; 536/23.1; 536/23.5

[58] Field of Search .................. 536/23.5, 23.1; 435/91.1, 91.51, 172.1, 172.3, 6

[56] References Cited

U.S. PATENT DOCUMENTS 5,482,845  1/1996  Soares et al. .................. 435/91.1

OTHER PUBLICATIONS

Patanjeli et al. Proc. Natl. Acad. Sci. USA 88 1943–1947 (1991) Construction of a uniform abundance (normalized) cDNA library.

Haraguchi et al. Proc. Natl. Acad. Sci. USA 84 412–415 (1987) Molecular cloning and nucleotide Sequence of cDNA for human . . .

*Primary Examiner*—James Ketter
*Assistant Examiner*—John S. Brusca
*Attorney, Agent, or Firm*—John P. White

[57] ABSTRACT

This invention provides a method to normalize a cDNA library constructed in a vector capable of being converted to single-stranded circles and capable of producing complementary nucleic acid molecules to the single-stranded circles comprising: (a) converting the cDNA library in single-stranded circles; (b) generating complementary nucleic acid molecules to the single-stranded circles; (c) hybridizing the single-stranded circles converted in step (a) with complementary nucleic acid molecules of step (b) to produce partial duplexes to an appropriate Cot; (e) separating the unhybridized single-stranded circles from the hybridized single-stranded circles, thereby generating a normalized cDNA library.

16 Claims, 1 Drawing Sheet

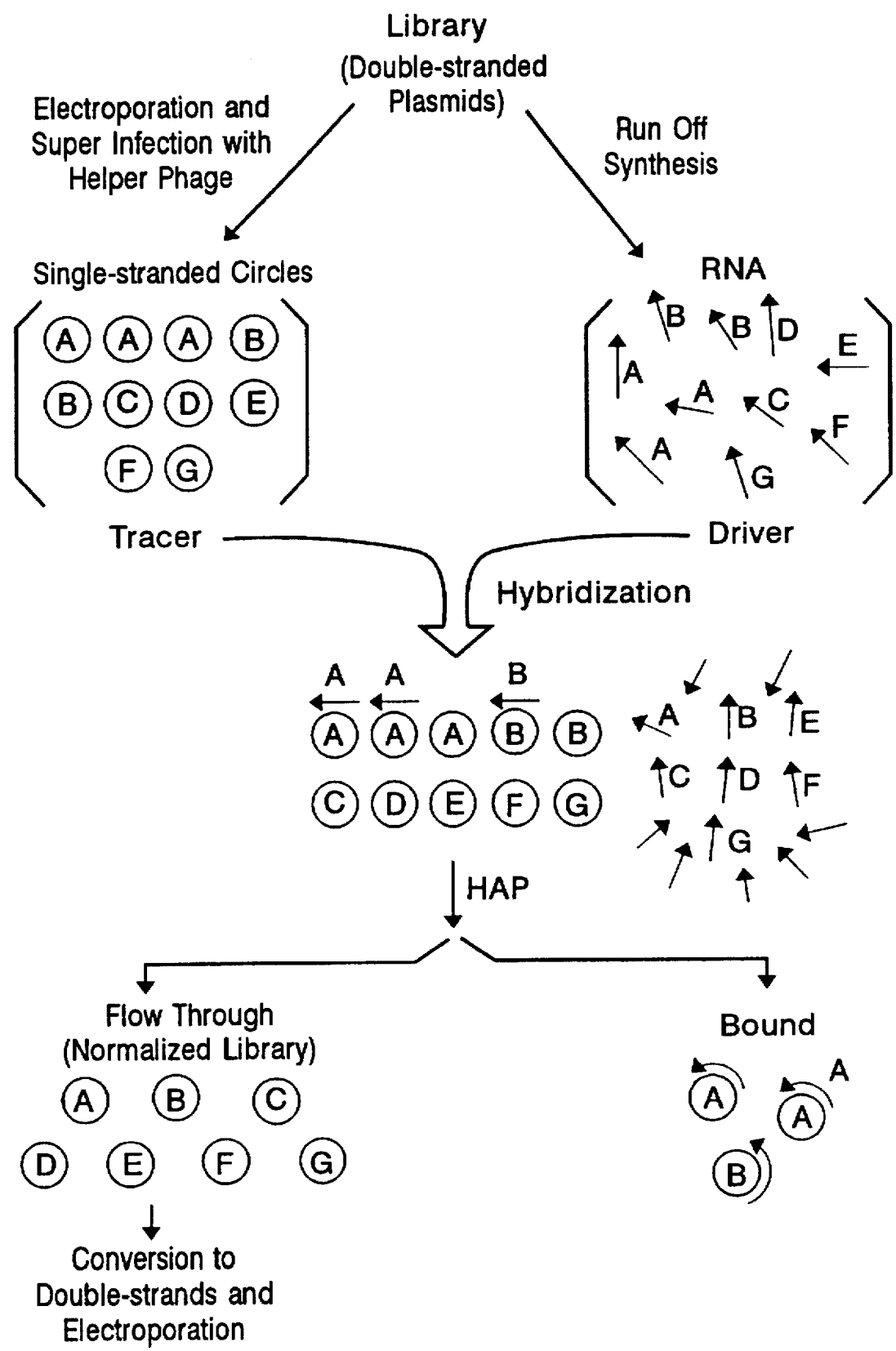

PROCEDURE FOR NORMALIZATION OF CDNA LIBRARIES

The invention disclosed herein was made with Government support under Grant No. R01-HG00980 from the National Institutes of Health, U.S. Department of Health and Human Services and Grant No. DE-FG02-91ER61233 from the U.S. Department of Energy. Accordingly, the U.S. Government has certain rights in this invention.

BACKGROUND OF THE INVENTION

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

To construct and partially characterize a number of directionally cloned, normalized, cDNA libraries from a variety of tissues and stages of development, each one of which with its unique sequence identifier.

The probability that a given mRNA will be represented in a cDNA library can be expressed by the equation $P(x)=1-(1-f)^n$, where f=frequency and n=number of recombinant clones. For example, the probability that the most rare mRNA (1 copy per cell or 1 in 500,000 total RNA molecules) will not be represented in a cDNA library of 5 million recombinants is $4.5 \times 10^{-5}$. Accordingly, although even the rarest mRNA is likely to be represented in such a library, its identification is very difficult (1/500,000). In a normalized cDNA library, however, the frequency of each clone is in the same narrow range. In average, normalization reduces the frequency of the most abundant clones by about 10 fold while increasing the frequency of the least prevalent cDNAs by approximately two fold.

Thus far, two approaches have been proposed to construct normalized cDNA libraries (Weissman, 1987). One approach is based on hybridization to genomic DNA. The frequency of each hybridized cDNA in the resulting normalized library would be proportional to that of each corresponding gene in the genomic DNA. The other is a kinetic approach: if cDNA reannealing follows second-order kinetics, rarer species anneal less rapidly and the remaining single-stranded fraction of cDNA becomes progressively more normalized during the course of the hybridization (Galau et al., 1977). Specific loss of any species of cDNA, regardless of its abundance, does not occur at any Cot value.

TABLE 1

Estimates of frequencies of brain mRNAs

|  | % mass | complexity (kb) | No. of RNA species |
|---|---|---|---|
| I. Superprevalent | 16% | 96 | 36 |
| II. Moderately prevalent | 46% | 5,800 | 2,150 |
| III. Complex | 38% | 122,000 | 45,000 |

|  | Frequency per species | Frequency per species at $C_0t = 5.5$ |
|---|---|---|
| I. Superprevalent | 0.44% | 0.02 |
| II. Moderately prevalent | 0.02% | 0.02 |
| III. Complex | 0.0008% | 0.0012 |

For the estimates of frequencies shown above, which should be regarded as rough but indicative, applicants used a set of reliable hybridization data that are available only for mouse brain mRNAs (Hahn et al., 1978), assuming that these measurements should not differ significantly among mammals [in all cases examined, including humans, the average amount of RNA per brain cell and the number of cells per gram of tissue are practically the same (see, e.g., Mandel et al., 1964; Winick, 1968)].

Applicants' calculations show (Soares et al., 1994) that, if a cDNA population is normalized by the kinetic approach, at a $C_0t=5.5$, of the three kinetic classes of mRNAs, the most abundant species are drastically diminished, while all frequencies are brought within the range of one order of magnitude (see Table above).

Methods to normalize cDNA libraries

Three groups have pursued independently the construction of normalized cDNA libraries based on the kinetic approach (Ko, 1990; Patanjali et al., 1991; Sasaki et al., 1994).

Ko (1990) reported the construction of a normalized mouse cDNA library by a complex scheme involving: (a) ligation of cDNAs to a linker-primer adaptor; (b) three rounds of PCR amplification, denaturation-reassociation, and purification of single stranded cDNAs by hydroxyapatite (HAP) column chromatography; (c) digestion of the end product using a site present in the linker-primer sequence and cloning (3' non coding cDNA fragments only) into a plasmid vector. Colony hybridization with eight probes of different abundances showed a reduction in abundance variation from at least 20,000 fold in the original library to 40-fold in the library constructed after three cycles of normalization.

In Ko's method, both coding and non coding fragments are present during reassociation. However, after the final digestion and directional cloning steps only the 3' non coding fragments remain in the normalized library.

Patanjali et al (1991) reported the construction of a normalized library by a similar method which involved: (a) cloning of short cDNAs produced by random priming into lgt10; (b) PCR amplification of cloned cDNAs; (c) denaturation and reassociation to moderate Cot; (d) separation of single-strands by HAP chromatography; (e) PCR amplification of HAP-flow-through single-stranded cDNAs; (f) cloning into lgt10.

Patanjali's normalized library consisted of cDNA clones containing both coding and non coding information. However, the cDNAs had to be relatively short and homogenous in length to assure equal efficiency of amplification during the polymerase chain reactions.

Sasaki et al (1994) described an alternative normalization procedure in which a cDNA library was constructed following depletion of abundant mRNA species by sequential cycles of hybridization of poly(A)+RNA to matrix-bound first-strand cDNA. After several cycles the depleted RNA was used for cDNA synthesis and cloning. The actual practical potential of this procedure still remains to be assessed, as the putative normalized library was not adequately characterized.

Applicants have developed a different method for normalization of directionally cloned cDNA libraries constructed in phagemid vectors which is based on the same kinetic principle (Soares et al., 1994; U.S. Ser. No. 08/126, 594). Briefly, a cDNA library in the form of single-stranded circles is annealed to a Not I-$(dT)_{18}$ oligonucleotide and controlled primer extension reactions are performed, with Klenow, in the presence of dNTPs and ddNTPs (except ddTTP) to yield products of about 160±20 nt nucleotides.

These partially double-stranded circles are purified from any remaining (unprimed) single-stranded circles by HAP column chromatography, desalted and then normalized by a kinetic approach, i.e. they are melted, reassociated to a $C_0t$ of 5–10 and the population that remains single-stranded (normalized library) is purified over HAP, desalted, partially converted to double-stranded circles by random priming and electroporated into bacteria.

The advantages of applicants' method can be outlined as follows: (a) because it does not require any cycle of cDNA amplification by the polymerase chain reaction, and therefore no length constraints are imposed, the cDNA clones in the normalized library constructed with applicants' protocol have large size inserts (average of 1.7 kb). Because the library is directionally cloned, the 3' end of a clone contains the 3' terminal exon of the mRNA, with a short polyadenylate track and a recognizable polyadenylation signal sequence at the appropriate position, whereas the 5' end of a clone almost always lie within coding sequence; (b) there is no cloning step involved in applicants' procedure, after completion of the reassociation reaction; (c) although the normalized library constructed according to applicants' protocol consists of clones that contain both coding and 3' non-coding exons, only 3' non-coding sequences participate in the reassociation reaction, thus addressing the problem raised by Ko (1990) regarding the potential cross hybridization, during the reaction of reassociation, between coding exons from gene family members that are represented at different frequencies in the original cDNA population, without however, having to sacrifice the quality of the normalized library by leaving behind all relevant coding sequence information.

SUMMARY OF THE INVENTION

This invention provides a method to normalize a cDNA library constructed in a vector capable of being converted to single-stranded circles and capable of producing complementary nucleic acid molecules to the single-stranded circles comprising: (a) converting the cDNA library in single-stranded circles; (b) generating complementary nucleic acid molecules to the single-stranded circles; (c) hybridizing the single-stranded circles converted in step (a) with complementary nucleic acid molecules of step (b) to produce partial duplexes to an appropriate Cot; (e) separating the unhybridized single-stranded circles from the hybridized single-stranded circles, thereby generating a normalized cDNA library.

BRIEF DESCRIPTION OF THE FIGURES

FIG. 1. An alternative approach to normalize cDNA libraries constructed in Phagemid Vectors.

DETAILED DESCRIPTION OF THE INVENTION

This invention provides a method to normalize a cDNA library constructed in a vector capable of being converted to single-stranded circles and capable of producing complementary nucleic acid molecules to the single-stranded circles comprising: (a) converting the cDNA library in single-stranded circles; (b) generating complementary nucleic acid molecules to the single-stranded circles; (c) hybridizing the single-stranded circles converted in step (a) with complementary nucleic acid molecules of step (b) to produce partial duplexes to an appropriate Cot; (e) separating the unhybridized single-stranded circles from the hybridized single-stranded circles, thereby generating a normalized cDNA library. In an embodiment, the cDNA library is a directional cDNA library. In another embodiment, the cDNA library is a randomly-primed cDNA library.

In an embodiment, the complementary nucleic acid molecules are in excess of the single-stranded circles. In a further embodiment, the complementary nucleic acid molecules are at least one hundred times in excess of the single-stranded circles.

In a preferred embodiment, the complementary nucleic acid molecules and the single-stranded circles are hybridized to a Cot of about five to fifty.

This invention also provides the above-described method wherein the hybridized single-stranded circles and the unhybridized single-stranded circles are separated by hydroxyapatite column chromatography.

In an embodiment, the unhybridized single-stranded circles are converted to double-stranded circles. In a further embodiment, the double-stranded circles are introduced into host cells.

This invention provides normalized cDNA libraries generated by the above-described methods. In an embodiment, wherein the cDNA is derived from a human placenta. In a separate embodiment, the cDNA is derived from human breast tissues. In a still separate embodiment, the cDNA is derived from pineal glands in human brain. In a further embodiment, the cDNA is derived from human retina tissues. In a still further embodiment, the cDNA is derived from ovarian tumor tissues.

This invention will be better understood from the Experimental Details which follow. However, one skilled in the art will readily appreciate that the specific methods and results discussed are merely illustrative of the invention as described more fully in the claims which follow thereafter.

Experimental Details

The method applicants originally developed to normalize directionally cloned cDNA libraries (Soares et al., 1994; U.S. Ser. No. 08/126,594) has been successfully utilized to generate libraries from infant brain and fetal liver-spleen. Both libraries were very extensively characterized by (a) colony hybridization with a number of cDNA probes representing mRNAs that occur at a wide range of frequencies in the tissues they were derived from, (b) by single-pass sequencing of a large number of clones, and (c) by Southern analysis (i.e., DNA from starting and normalized libraries were digested, Southern transferred to a nylon membrane and hybridized with a number of cDNA probes to assess whether normalization favored smaller versus larger cDNAs). Altogether these experiments demonstrated very consistently that the normalization procedure was very effective to bring the frequencies of cDNA clones to within a narrow range.

Applicants have found, however, that in libraries normalized by applicants' original method (Soares et al., 1994), if a given mRNA is represented by two different but overlapping cDNA clones such that one is full-length and the other corresponds to a 3' truncation (i.e., it resulted from an internal priming event and therefore is missing the 3' most of the mRNA), the latter is favored over the former. This phenomenon is a result of the fact that in applicants' original procedure there is a 1:1 ratio between circles and hybridizing extension products. Accordingly, while the extension product of the full-length clone can only reassociate to its very own template, i.e. the full-length single-stranded circle, the extension product of the 3' truncated clone can reassociate to either its very own template, i.e. the 3' truncated single-stranded circle, or to the full-length single-stranded circle. Since the truncated circle occurs at a lower frequency, the most likely outcome is that the extension product derived from the truncated circle reassociates to the full-length circle, simply because the latter is represented at a higher frequency in the library. Consequently, the truncated circle is more likely to remain as single-stranded and therefore to end up in the flow-through of the HAP column (normalized library). It should be emphasized, however, that this problem only happens in those cases where truncations occur. Applicants have documented this problem by Southern analysis of the starting and normalized infant brain libraries with a 16S mitochondrial rRNA probe. The predominant species in the starting library, which was the longest hybridizing fragment, was practically absent from the normalized library whereas the smaller fragments, which were not as prevalent in the starting library, increased in frequency with normalization. This was ultimately demonstrated by sequencing analysis of a number of 16S mitochondrial rRNA clones from both the starting and normalized infant brain libraries.

The solution to this problem is to use an excess of hybridizing fragments to avoid competition between full-length and truncated clones. Applicants have successfully addressed this problem in applicants' new procedure, by replacing the short extension products used in applicants' original method with in vitro synthesized RNA, which is used in excess to, rather than in equimolar amounts to, single-stranded circles. Because the RNA is in excess over the DNA, its concentration essentially remains unchanged throughout the reaction, which therefore follows pseudo-first-order kinetics, as opposed to second-order kinetics as it was the case for applicants' original method. Applicants have documented by Southern analysis that this modification has been successful to correct this problem.

An improved method to normalize cDNA libraries

Following is a brief description of the alternative approach that applicants have developed for normalization of cDNA libraries.

Plasmid DNA from a library cloned in the pT7T3-Pac vector (a modification of the commercially available pT7T3 vector, Pharmacia) is linearized with one of the cloning sites (Eco RI), or with a flanking restriction site, and antisense run-off RNA is synthesized in vitro from the T3 promoter. This RNA, in large excess over the single-stranded circles, is then hybridized to the cDNA library in the form of single-stranded circles to a Cot of 5–50 and the unreassociated single-strands are isolated by HAP chromatography, partially converted into duplexes by random primed synthesis and electroporated into bacteria.

This method has the following advantages: first of all, as mentioned above, because an excess of RNA is used, there is no competition between full-length and truncated versions for complementary fragments and therefore there is no bias against longer clones. Second of all, since the synthesis is driven by an RNA promoter, even those clones without tail will be represented in the normalized library. Third of all, since the driver concentration is high, a Cot of 5–50 can be achieved in a few hours of incubation, thus making the procedure much quicker. Last, but not least, only one (as opposed to two) step of HAP purification is required, thus making the procedure considerably simpler and quicker.

Human fetal liver-spleen RNA was used for construction of normalized cDNA libraries by the original ([1]Nb[2]HFLS20W) and alternative ([2]Nb[2]HFLS20W) procedures. They were both characterized by colony hybridization with a number of cDNA probes. The results of this comparative analysis are shown below.

TABLE 2

COMPARISON OF TWO NORMALIZED HUMAN FETAL LIVER-SPLEEN cDNA LIBRARIES

| | STARTING LIBRARY (b[2]HFLS20) | NORMALIZED BY THE ORIGINAL METHOD ([1]Nb[2]HFLS20) |
|---|---|---|
| ALBUMIN | 4% (87/2,222) | 0.3% (2/598) |
| APOLIPOPROTEIN A1 | 1% (51/5,000) | 0.2% (1/598) |
| FERRITIN | 1% (2/202) | 0.2% (1/598) |
| SUB 3 (unknown) | 0.01% (4/60,000) | 0.02% (14/60,000) |
| RIBOSOMAL PTN S20 | 0.1% (4/5,000) | not determined |
| ANGIOTENSINOGEN | 0.2% (10/5,000) | not determined |
| ALDOLASE | 0.4% (22/5,000) | not determined |
| TRANSLATIONALLY CONTROLLED TUMOR PROTEIN | not determined | not determined |
| MOUSE STERILITY COMPLEX | 0.02% (0/5,000) | not determined |

| | NORMALIZED BY THE ALTERNATIVE APPROACH ([2]Nb[2]HFLS20) |
|---|---|
| ALBUMIN | 0.4% (4/1,121) |
| APOLIPOPROTEIN A1 | 0.2% (2/1,121) |
| FERRITIN | 0.3% (3/1,121) |
| SUB 3 (unknown) | not determined |
| RIBOSOMAL PTN S20 | 0.01% (3/50,000) |
| ANGIOTENSINOGEN | 0.1% (46/50,000) |
| ALDOLASE | 0.03% (13/50,000) |
| TRANSLATIONALLY CONTROLLED TUMOR PROTEIN | 0.02% (8/50,000) |
| MOUSE STERILITY COMPLEX | 0.01% (4/50,000) |

Applicants have also constructed a normalized retina library according to applicants' alternative approach. Following are the results of the colony hybridization experiments that were performed for assessment of normalization.

TABLE 3

COLONY HYBRIDIZATION OF STARTING AND NORMALIZED RETINA-1723 LIBRARIES WITH EIGHT cDNA

| cDNA PROBE | STARTING LIBRARY | NORMALIZED LIBRARY |
|---|---|---|
| Neurofilament subunit NF-L (NNR3FO5) | 2% (7/360) | 0.04% (2/5445) |
| elongation factor 1a | 0.5% (25/5,000) | 0.1% (32/50,000) |
| b[3]HR1723-Bound 48 Drosophila fat facet | 0.2% (8/5,000) | 0.01% (6/50,000) |
| b[3]HR2430-5 (unknown) | 0.01% (10/104,100) | 0.02% (7/47,250) |
| b[3]HR1723-12 (unknown) | 0.03% (28/104,100) | 0.01% (3/47,250) |
| giantin | 0.04% (2/5,000) | 0.01% (6/50,000) |
| mitochondrial 16SrRNA | <0.28% (0/360) | 0.1% (5/5445) |
| b[3]HR1723-Bound 72 mitogen (mig2) | 0.02% (1/5,000) | 0.02% (9/50,000) |
| frequency variation | 200 | 10 |

In addition to the fetal liver-spleen and retina libraries (Tables 4 and 5), applicants have also successfully used this protocol to construct normalized libraries from human adult brain, adult hippocampus and placenta. No bias towards smaller clones could be detected so far. For example, the same problem observed with the 16S rRNA in the infant brain library (see discussion above) has been observed for albumin in the liver-spleen library constructed according to applicants' original protocol. The full-length insert absent from the normalized library whereas smaller truncated cDNAs were at the same or high frequency in the normalized library, as compared to the starting library. However, this problem did not happen when the same fetal liver-spleen library was normalized by the new alternative procedure. The full-length albumin decreased in frequency, as it should have, just as the smaller albumin cDNA clones did, but they all remained represented in the normalized library.

TABLE 4

Colony hybridization of starting and normalized retina-1723 libraries with five cDNA probes.

| cDNA probe | Starting Library ($b^3$HR1723) | HAP-FT (NORMALIZED) |
|---|---|---|
| Glutamine synthase | 0.55% (2/360) | 0.09% (5/5445) |
| mitochondrial 16SrRNA | <0.28% (0/360) | 0.09% (5/5445) |
| NNR3FO5 (unknown) | 1.94% (7/360) | 0.04% (2/5445) |
| $b^3$HR2430-5 (unknown) | 0.01% (10/104,100) | 0.015% (7/47,250) |
| $b^3b^3$HR1723-12 (unknown) | 0.03% (28/104,100) | 0.01% (3/47,250) |
| frequency variation | 194 | 9 |

| cDNA probe | HAP-BOUND |
|---|---|
| Glutamine synthase | 0.8% (8/990) |
| mitochondrial 16SrRNA | .01% (1/990) |
| NNR3FO5 (unknown) | 8.1% (80/990) |
| $b^3$HR2430-5 (unknown) | <0.1% (0/990) |
| $b^3$HR1723-12 (unknown) frequency variation | |

TABLE 5

Colony hybridization of starting and normalized retina-2430 libraries with five cDNA probes.

| cDNA probe | Starting Library ($b^3$HR2430) | HAP-FT (NORMALIZED) |
|---|---|---|
| Glutamine synthase | 0.8% (14/1793) | 0.07% (10/14036) |
| mitochondrial 16SrRNA | 0.2% (4/1793) | 0.06% (9/14036) |
| NNR3FO5 (unknown) | 2.8% (50/1793) | 0.16% (23/14036) |
| $b^3$HR2430-5 (unknown) | 0.01% (3/42,500) | 0.02% (8/46,250) |
| $b^3$HR1723-12 (unknown) | 0.02% (7/42,500) | 0.02% (11/46,250) |
| frequency variation | 280 | 8 |

| cDNA probe | HAP-BOUND |
|---|---|
| Glutamine synthase | 0.4% (8/1848) |
| mitochondrial 16SrRNA | .3% (6/1848) |
| NNR3FO5 (unknown) | 4.7% (87/1848) |
| $b^3$HR2430-5 (unknown) | <0.05 (0/1848) |
| $b^3$HR1723-12 (unknown) frequency variation | |

Reaction conditions:
driver concentration: 10 µg/12.5 µl reaction
tracer concentration: 12.5 ng/12.5 µl reaction
reaction time: 1 h
$C_0t = 12$ cDNA Library Construction Applicants intend to generate a collection of tagged normalized cDNA libraries from a variety of tissues and stages of development of valued organisms in which a significant fraction of all genes are expected to be represented.

cDNA synthesis and cloning are performed essentially as described (Soares, 1994). Briefly, poly(A) RNA is annealed to a Not-oligo(dT) primer under controlled conditions to avoid, to the extent possible, internal priming events [such non specific priming events can be easily recognized as clones containing a tail at the 3' end but no polyadenylation signal sequence at the appropriate distance upstream] and 1st strand cDNA is synthesized at 37° C. using RNAse H⁻ Reverse Transcriptase (Superscript II, BRL) in the presence of 0.5 mM each dNTP. Second-strand cDNA is synthesized by nick translation in a reaction containing *E.coli* DNA Polymerase I, RNAse H and *E.coli* DNA Ligase. Double-stranded cDNA is polished with T4 DNA Polymerase, size fractionated by chromatography over a 64 cm long and 0.2 cm wide Biogel A50 column and ligated to Eco RI adaptors (1,00 fold excess). After digestion with Not I, cDNAs are size selected once again over a Biogel A50 column, phosphorylated and ligated to a 1.5 molar excess of a phagemid vector (pT7T3, Pharmacia, with a modified polylinker, doubly digested with Not I and Eco RI). For vector preparation, CsCl banded plasmid DNA is doubly digested with Not I+Eco RI, gel purified, digested with Bam HI (which is located in the polylinker between the Not I and Eco RI sites), and purified over a 5 ml Sepharose 4B column pre-equilibrated with 0.4M NaCl in TE (10 mM Tris, 1 mM EDTA). Control ligations, which are routinely performed to assess the quality of the vector, indicate that this procedure is very reliable to yield vectors with background levels of the order of $10^4$ colonies/mg.

The ligated material is phenol/Sevag extracted, ethanol precipitated, electroporated into "home made" competent DH10B (BRL) bacteria and inoculated into 250 mls of media. A small aliquot of this culture is plated on an agar plate containing ampicillin after 1 h of incubation at 37° C., for assessment of number of primary recombinants. Ampicillin (75 mg/ml) is then added to the culture which is then incubated at 37° C. under vigorous agitation for 8–12 h. Plasmid DNA is prepared using a Qiagen Midi Size column and as a first quality check a small sample of it is electrophoresed on an agarose minigel next to supercoiled pT7T3 vector. If the library is of good quality, there should be a good separation between the empty vector and the lower portion of the library smear.

If necessary, the following additional purification step can be pursued at this point. Plasmid DNA representing the entire library is linearized with Not I, electrophoresed on an agarose gel, the upper most of the smear is cut out of the gel, casted into a low melting agarose gel, run backwards until sharpened, and DNA is purified using beta agarase. After recircularization in a large volume ligation reaction, plasmid DNA is extracted with phenol/Sevag, ethanol precipitated and electroporated into bacteria.

Typically, libraries of 1–5 million recombinants are obtained from 0.5 mg of poly(A)+RNA according to this protocol. Insert sizes average 1.7 kb, but range from 0.5 kb to 4 kb and the frequency of non recombinant clones is very low (e.g., one out of 1,500 randomly picked clones from a normalized infant brain library; none out of 1,000 sequences from the fetal liver-spleen library).

Applicants have optimized primer concentration and annealing conditions to achieve saturation of the poly(A) tail and thereby generate clones that have short oligo(A) tracks at their 3' end, thus facilitating sequencing from the 3' end. This is possible because reverse transcriptase cannot strand displace. Consequently, by saturating the tail with primers, only the one that is the closest to the beginning of the poly(A) tail of the mRNA is extended into a long product. All other primers are extended for a short distance and synthesis stops when the growing chain encounters the next primer ahead. Combined with an efficient procedure to size fractionate cDNAs (see below), which successfully eliminates all these short double-stranded fragments of tail, this strategy has proven very reliable to generate clones with short tail. This has been solidly documented by sequencing analysis of thousands of cDNA clones randomly picked from libraries that applicants constructed according to these protocols (see for example Adams et al., 1993).

In order to provide an unique identifier, or sequence tag, a different oligonucleotide is used to prime the synthesis of 1st strand cDNA for each library that is constructed. These oligonucleotides have about 20 bases upstream from the Not I site, to provide enough footing for Not I to digest the double-stranded cDNA efficiently, and a sequence tag of 3–6 nucleotides between the Not I site and the stretch of oligo $(dT)_{18}$.

cDNA Library Normalization

All cDNA libraries will be normalized according to the alternative approach described in the Preliminary Data Section (Bonaldo & Soares, manuscript in preparation). Briefly, plasmid DNA from the entire library is linearized with Eco RI and/or Xho I (the latter is located in the polylinker immediately next to the Eco RI site) and antisense RNA is synthesized in vitro off the T3 promoter. After treatment with RNAse free-DNAse I, the RNA is annealed to a blocking oligonucleotide (its sequence is complementary to the sequence of the RNA that corresponds to vector and mRNA tail) and hybridized ($C_0t=10$) to the library itself in the form of single-stranded circles. The unhybridized fraction (normalized library) is purified from the heteroduplexes by hydroxyapatite column chromatography, desalted through a Nensorb column (DuPont), partially converted to double-stranded circles by random priming and electroporated into competent DH10B bacteria.

Partial Characterization for Quality Assessment

As a routine libraries are characterized by three approaches: (a) colony hybridization, (b) Southern analysis, and (c) single-pass sequencing of a limited number of clones.

(a) Colony Hybridization. Typically, the normalization procedure successfully reduces the frequency of the most prevalent mRNAs by about 10–100 fold. Accordingly, the most indicative experiment to ascertain whether normalization has been achieved consists of screening both the starting and putatively normalized cDNA libraries with a few cDNA probes derived from the most abundant transcripts [cDNA clones from abundant transcripts can be easily obtained from the HAP-bound fraction, see below]. If the results indicate that normalization might have been successful, a second round of colony hybridization experiments is then performed, this time with cDNA probes derived from intermediate and low abundance transcripts, to demonstrate that in the normalized library, in contrast to the starting library, the frequencies of all clones is within a narrow range. (b) Southern analysis. In order to verify that cDNA insert sizes are the same in both starting and normalized libraries, plasmid DNA from both sources is digested with Not I+Eco RI, electrophoresed on an agarose gel, Southern transferred to a nylon membrane and sequentially hybridized with the same cDNA probes used for the colony hybridization experiments. This experiment has proven very effective to address this issue at the same time that it also provides an indication of abundance variation of specific cDNA clones in both starting and normalized libraries.

(c) Sequencing analysis. Applicants have been routinely performing single-pass sequencing and database search analysis of a sample of clones randomly picked from each starting, HAP flow-through (normalized) and HAP-bound libraries. This serves the following purposes: (1) to verify that cDNA inserts have been directionally cloned, that their 3' tails are short and present in most clones, and that the expected sequence tag can be observed; (2) to quickly identify cDNA clones derived from abundant transcripts to be used as probes for the colony hybridization experiments described above. This can be achieved by sequencing 50–100 clones of the HAP-bound library. As discussed above, the normalization procedure is essentially a kinetic approach in which cDNAs are melted and allowed to reassociate to a relatively low $C_0t$ of 10. The fraction that remains single-stranded (the normalized library) is then purified from the hybridized material by HAP chromatography (i.e., the former flows through the column whereas the latter binds). Therefore cDNA clones derived from abundant mRNAs, which are present at a high frequency in the starting library, are expected to be present at an even higher frequency in the HAP-bound fraction. Accordingly, they should be easily identified by random sequencing of a relatively small sample of clones from the HAP-bound library. As a routine, applicants have been sequencing about 100 clones from each HAP-bound library and applicants' results indicate that this approach is always successful to quickly identify the most abundant transcripts from any given tissue source.

REFERENCES

Adams, M. D., Soares, M. B., Kerlavage, A. R., Fields, C. and Craig Venter, J. (1993). Rapid cDNA sequencing from a directionally cloned human infant brain cDNA library. Nature Genet. 4, 373–380.

Chomcznski, P. and Sacchi, N. (1987). Single-step method of RNA isolation by acid guanidinium thiocyanate-phenol-chloroform extraction. Analyt. Biochem. 162, 156–159. Hahn, W. E., Van Ness, J. & Maxwell, I. E. (1978). Proc. Natl. Acad. Sci. USA 75, 5544–5547.

Ko, M. S. H. (1990). Nucleic Acids Res. 18, 5705–5711. Mandel, P., Rein, H., Harth-Edel, S. & Mardell, R. (1964). In Comparative Neurochemistry, ed. Richter, D. (Macmillan, New York), pp. 149–163.

Patanjali, S. R., Parimoo, S. & Weissman, S. M. (1991). Proc. Natl. Acad. Sci. USA 88, 1943–1947.

Sambrook, J., Fritsch, E. F. and Maniatis, T. (1989). Molecular cloning: a laboratory manual. Cold Spring Harbor Laboratory Press, Cold Spring Harbor, N.Y.

Soares, M. B. (1994). Construction of directionally cloned cDNA libraries in phagemid vectors. In "Automated DNA Sequencing and Analysis Techniques." M. D. Adams, C. Fields & J. Craig Venter (Eds.), pp.110–114, Academic Press, London.

Weissman, S. M. (1987). Mol. Biol. Med. 4, 133–143.

Winick, M. (1968). Pediatr. Res. 2, 352–355.

What is claimed is:

1. A method to normalize a cDNA library constructed in a vector capable of being converted to single-stranded circles and capable of producing complementary nucleic acid molecules to the single-stranded circles comprising:

(a) converting the cDNA library to single-stranded circles;

(b) generating antisense RNA in vitro to the single-stranded circles;

(c) hybridizing the single-stranded circles converted in step (a) with antisense RNA of step (b) to produce partial duplexes to an appropriate Cot; and (d) purifying the unhybridized single-stranded circles from the hybridized single-stranded circles, thereby generating a normalized cDNA library.

2. The method of claim 1, wherein the cDNA library is a directional cDNA library.

3. The method of claim 1, wherein the cDNA library is a randomly-primed cDNA library.

4. The method of claim 1, wherein the cDNA library is constructed in the pT7T3-Pac vector.

5. The method of claim 1, wherein the antisense RNA is in excess of the single-stranded circles.

6. The method of claim 3, wherein the antisense RNA is at least one hundred times in excess of the single stranded circles.

7. The method of claim 1, wherein the antisense RNA and the single-stranded circles are hybridized to a Cot of about five to fifty.

8. The method of claim 1, wherein the unhybridized single-stranded circles are purified from the hybridized single stranded circles by hydroxyapatite column chromatography.

9. The method of claim 1, further comprising introducing the unhybridized single-stranded circles into host cells.

10. The method of claim 9, further comprising conversion of the unhybridized single-stranded circles into double-stranded DNA circles before the introduction into the hosts.

11. A normalized cDNA library generated by the method of claim 1.

12. A library of claim 11, wherein the cDNA is derived from a human placenta.

13. A library of claim 11, wherein the cDNA is derived from human breast tissues.

14. A library of claim 11, wherein the cDNA is derived from pineal glands in human brain.

15. A library of claim 11, wherein the cDNA is derived from human retina tissues.

16. A library of claim 11, wherein the cDNA is derived from ovarian tumor tissues.

* * * * *